United States Patent [19]

Braish

[11] Patent Number: 5,082,970
[45] Date of Patent: Jan. 21, 1992

[54] PROCESS FOR RECYCLING AMINE ISOMER

[75] Inventor: Tamim F. Braish, Ledyard, Conn.

[73] Assignee: Pfizer Inc., New York, N.Y.

[21] Appl. No.: 665,506

[22] Filed: Mar. 6, 1991

[51] Int. Cl.$^5$ .......................................... C07C 209/88
[52] U.S. Cl. .................... 564/424; 564/307; 564/308; 564/425; 564/428
[58] Field of Search ............... 564/308, 307, 424, 425, 564/428; 568/308

[56] References Cited

U.S. PATENT DOCUMENTS

| | | | |
|---|---|---|---|
| 3,506,714 | 4/1970 | Hinkley et al. | 260/590 |
| 4,463,176 | 7/1984 | Dennis et al. | 546/208 |
| 4,536,518 | 8/1985 | Welch, Jr. et al. | 514/647 |
| 4,556,676 | 12/1985 | Welch, Jr. et al. | 514/554 |

Primary Examiner—Richard L. Raymond
Assistant Examiner—Brian M. Burn
Attorney, Agent, or Firm—Peter C. Richardson; Paul H. Ginsburg

[57] ABSTRACT

A novel process for converting trans-isomeric N-methyl-4-(3,4-dichlorophenyl)-1,2,3,4-tetrahydro-1-naphthaleneamine to cis-isomeric N-methyl-4-(3,4-dichlorophenyl)-1,2,3,4-tetrahydro-1-naphthaleneamine is disclosed. The process involves contacting trans-isomeric N-methyl-4-(3,4-dichlorophenyl)-1,2,3,4-tetrahydro-1-naphthaleneamine, or a mixture of same with up to about an equal part by weight of the corresponding cis-isomer, with a basic equilibration agent like potassium tert.-butoxide in a reaction-inert polar organic solvent to ultimately afford a cis/trans-mixture wherein the amount of cis-amine present in said mixture achieves a constant value of about 2:1 on a weight-by-weight basis. The aforesaid resultant mixture is useful as an intermediate product that ultimately leads to pure cis-(1S) (4S)-N-methyl-4-(3,4-dichlorophenyl)-1,2,3,4-tetrahydro-1-naphthaleneamine (sertraline), which is a known antidepressant agent.

23 Claims, No Drawings

PROCESS FOR RECYCLING AMINE ISOMER

TECHNICAL FIELD

This invention relates to a process for recycling a trans-amine to a cis-amine. More particularly, it is concerned with a novel method for converting trans-isomeric N-methyl-4-(3,4-dichlorophenyl)-1,2,3,4-tetrahydro-1-naphthaleneamine to the corresponding cis-isomeric product. The latter material is useful as an intermediate that ultimately leads to the antidepressant agent known as cis-(1S)(4S)-N-methyl-4-(3,4-dichlorophenyl)-1,2,3,4-tetrahydro-1-naphthaleneamine (sertraline).

BACKGROUND ART

There is described in U.S. Pat. Nos. 4,536,518 and 4,556,676 to W. M. Welch, Jr. et al., as well as in the paper of W. M. Welch, Jr. et al., appearing in the *Journal of Medicinal Chemistry*, Vol. 27, No. 11, p. 1508 (1984), a multi-step method for synthesizing pure racemic cis-(1S)(4S)-N-methyl-4-(3,4-dichlorophenyl)-1,2,3,4-tetrahydro-1-naphthaleneamine, starting from the readily available 3,4-dichlorobenzophenone. In the last step of this synthesis, N-[4 -(3,4 -dichlorophenyl) -3,4-dihydro-1(2H) -naphthalenylidene]methenamine is reduced by means of catalytic hydrogenation or by the use of a metal hydride complex to N-methyl-4-(3,4-dichlorophenyl)-1,2,3,4-tetrahydro-1-naphthaleneamine, which is actually a mixture of the cis- and trans-isomers in the form of a racemate. The aforesaid isomeric mixture is then separated into its component parts by conventional means, e.g., by fractional crystallization of the hydrochloride salts or by column chromatography on silica gel of the corresponding free base. Resolution of the separated cis- racemate free base compound while in solution with an optically-active selective precipitant acid, such as D-(—)-mandelic acid, in a classical manner then ultimately affords the desired cis-(1S)(4S)-enantiomer (sertraline).

Nevertheless, the above described production of pure cis-(1S)(4S)-N-methyl-4-(3,4-dichlorophenyl)-1,2,3,4-tetrahydro- 1-naphthaleneamine is disadvantageous in that large amounts of the unwanted racemic trans-isomer (which ultimately leads to the unwanted trans-(1S)(4R)-enantiomer) are co-produced and must eventually be discarded, thereby lowering the overall yield of the desired cis-(1S)(4S)-enantiomer and increasing the costs of production. Therefore, it is an object of the present invention to utilize the unwanted trans-isomer that is co-produced in the aforesaid synthesis and so lower the total costs of production. Another and more specific object of the present invention is to convert the aforesaid trans-racemate free base to the corresponding cis-isomer and thereby, in effect, recycle the previously unwanted trans-isomer back into the present method of production for the desired cis-isomer. Still another and even more specific object of the present invention is to convert the previously unwanted chiral trans-(1S)(4R)-isomer into the corresponding chiral cis-(1S)(4S)-isomer which is, of course, sertraline.

DISCLOSURE OF THE INVENTION

In accordance with the present invention, there is now provided a process for converting trans-isomeric N-methyl-4-(3,4-dichlorophenyl)-1,2,3,4-tetrahydro-1-naphthaleneamine to cis-isomeric N-methyl-4-(3,4-dichlorophenyl)-1,2,3,4-tetrahydro-1-naphthaleneamine, said process comprising contacting trans-isomeric N-methyl-4-(3,4-dichlorophenyl)-1,2,3,4-tetrahydro-1-naphthaleneamine in the absence or presence of up to about an equal part by weight of the corresponding cis-isomer with a basic equilibration agent, such as 1,3-diazabicyclo[5.4.0]undec-7-ene or an alkali metal lower alkoxide ($C_1$-$C_4$) like potassium tert.-butoxide, in a reaction-inert polar organic solvent system at a temperature that is in the range of from about 55° C. up to about 125° C. until the amount of the desired cis-amine in the resultant cis/trans-mixture achieves a constant value of about 2:1 on a weight-by-weight basis. In this connection, it is to be understood that by the use of the term trans-isomeric N-methyl-4-(3,4-dichlorophenyl)-1,2,3,4-tetrahydro-1-naphthaleneamine there is meant to be included not only the racemic trans-compound, but also the corresponding chiral trans-(1S)(4R)-enantiomer which is easily derived from same via resolution with L-(+)-mandelic acid and was first reported by W. M. Welch, Jr. et al. in the aforementioned *Journal of Medicinal Chemistry* reference article.

More specifically, by the use of the process of this invention, a recycled starting material such as pure racemic trans-N-methyl-4-(3,4-dichlorophenyl)-1,2,3,4-tetrahydro-1-naphthaleneamine or a 1:1by weight mixture of said trans-isomer with the corresponding cis-isomer is converted to about a 2:1 by weight cis/trans-mixture of the isomers in a most facile manner. As previously indicated, the latter 2:1 resultant mixture is useful as an intermediate product that leads to pure cis-(1S)(4S)-N-methyl-4-(3,4-dichlorophenyl)-1,2,3,4-tetrahydro-1-naphthaleneamine (sertraline), which is a known antidepressant agent. In like manner, chiral trans-(1S) (4R)-N-methyl-4-(3,4-dichlorophenyl)-1,2,3,4-tetrahydrophenyl-1-naphthaleneamine or a 1:1 by weight mixture of said trans-isomer with the corresponding cis-isomer (viz., the chiral cis-(1S)(4S)-enantiomer) is also converted to about a 2:1 by weight cis/trans-mixture of the isomers in a most facile manner. However, in the latter case, the resultant 2:1 cis/trans-mixture of chiral isomers leads directly to sertraline since the resolution step is no longer required.

DETAILED DESCRIPTION OF THE INVENTION

In accordance with the process of this invention, the equilibration reaction is generally carried out by using an excess in moles of the basic equilibration agent with respect to the total amount of N-methyl-4-(3,4-dichlorophenyl)-1,2,3,4-tetrahydro-1-naphthaleneamine starting material (i.e., trans-isomer with up to about an equal part by weight of the cis-isomer, etc.) and preferably by using at least about one mole of said starting material per mole of the basic equilibration agent, with the most preferred range being from about 1.0:1.0 to about 1.0:2.0, in order to effect the desired conversion of the trans-isomer to the cis-isomer as previously discussed. The process is normally conducted in a reaction-inert polar organic solvent system at a temperature that is in the range of from about 55° C. up to about 125° C., and preferably one that is in the range of from about 65° C. up to about 90° C., until the desired conversion to the constant 2:1 (by weight) cis/trans-mixture is substantially complete. Generally, the equilibration reaction will require a time period of at least about four hours, although it is preferable in practice to carry out the reaction for a period of about 40 hours. Preferred reaction-inert polar organic solvents for use in this connection include lower dialkyl ($C_1$-$C_4$) ethers having a total of at least five carbon atoms such as di-isopropyl ether, di-n-butyl ether, methyl n-butyl ether and ethyl isopropyl ether, cyclic ethers such as tetrahydrofuran and dioxane, alkylated glycols having a total of from four to eight carbon atoms, like 1,1-diethoxymethane, 1,2-dimethoxyethane, 2-ethoxyethanol, 2-n-butoxyethanol, the dimethyl ether of butylene glycol and the di-n-propyl ether of ethylene glycol, as well as lower N,N-dialkyl lower alkanoamides having a total of up to six carbon atoms (with at least one of said atoms always being present in the N,N-unsubstituted alkanoamide moiety) like dimethylformamide, diethylformamide, dimethylacetamide, diethylacetamide, dimethylpropionamide and so forth. Preferred basic equilibration agents employed for purposes of the invention process include 1,8-diazabicyclo[5.4.0]undec-7-ene, 1,5-diazabicyclo[4.3.0]non-5-ene, 1,4-diazabicyclo[2.2.2]-octane, lithium di-isopropylamide and lithium tetramethylpiperidide, as well as various metal lower alkoxides ($C_1$-$C_4$) like the alkali metal lower alkoxides ($C_1$-$C_4$), such as sodium ethoxide and potassium tert.-butoxide. Optimum results are generally obtained when dimethylformamide and like alkanoamide solvents are employed in conjunction with the first-three named basic equilibration agents, and tetrahydrofuran and the other ether-type solvents are used in conjunction with the remaining basic equilibration agents, such as potassium tert.-butoxide and the like. In the latter connection, especially when tetrahydrofuran is employed as the solvent of choice in conjunction with the alkoxide-type equilibration agent, it has often been found most convenient and advantageous in practice to use small amounts of the corresponding lower alkanol in order to "spike" the aforesaid ethereal solvent and so aid in further increasing the solubility of the starting materials and final products that are contained within the selected solvent system. Usually, a minor amount of the alkanol "spike," say, for example, 5% by volume based on the total volume of the ethereal solvent, is sufficient for such purposes.

Upon completion of the equilibration reaction, the desired product, viz., pure racemic cis-N-methyl-4-(3,4-dichlorophenyl)-1,2,3,4-tetrahydro-1-naphthaleneamine or the pure chiral cis-(1S)(4S)-enantiomer thereof (as the case may be), is readily recovered from the reaction mixture by conventional means such as, for example, by first removing the solvent via evaporation under reduced pressure and then dissolving the resultant residue in a chlorinated lower hydrocarbon solvent such as methylene chloride, ethylene dichloride, s-tetrachlorethane, chloroform or carbon tetrachloride, followed by successive washing and drying of the resulting solution and subsequent evaporation of the solvent under reduced pressure to afford the previously discussed 2:1 (by weight) cis/trans-mixture (as detected by such analytical methods as thin layer chromatography, high pressure liquid chromatography, nuclear magnetic resonance spectroscopy, etc.) as the residual oil. When the latter oil is thereafter dissolved in an ethereal solvent such as tetrahydrofuran and treated with a dry hydrohalide gas, like anhydrous hydrogen chloride, the desired cis-amine precipitates from solution as the crystalline hydrohalide salt while the corresponding trans-amine salt remains in solution. In this way, a starting material such as unwanted racemic trans-N-methyl-4-(3,4-dichlorophenyl)-1,2,3,4-tetrahydro-1-naphthaleneamine or a 1:1(by weight) mixture of same with the desired cis-isomer is conveniently converted to pure crystalline racemic cis-N-methyl-4-(3,4-dichlorophenyl)-1,2,3,4-tetrahydro-1-naphthaleneamine hydrochloride via the aforesaid 2:1 (by weight) cis/trans-mixture. In like manner, the unwanted chiral trans-(1S)(4R)-enantiomer is converted to the desired chiral cis-(1S)(4S)-enantiomer, viz., cis-(1S)(4S)-N-methyl-4-(3,4-dichlorophenyl)-1,2,3,4-tetrahydro-1-naphthaleneamine hydrochloride, as previously discussed.

The pure racemic trans-N-methyl-4-(3,4-dichlorophenyl)-1,2,3,4-tetrahydro-1-naphthaleneamine starting material that may be used for conducting the equilibration process of this invention, as well as the desired pure racemic cis-amine final product are both reported as hydrochloride salts in the paper by W. M. Welch, Jr., as described in the *Journal of Medicinal Chemistry*, Vol. 27, No. 11, p. 1508 (1984), along with the corresponding free base compounds and an approximately 1:1 (by weight) mixture of the racemic cis- and trans-isomers (as the free amine base compounds) in crude form. The pure racemic cis-amine hydrochloride is also reported in U.S. Pat. No. 4,536,518 to W. M. Welch, Jr. et al., along with crude mixtures of the two isomers as hydrochloride salts, while the pure racemic trans-amine hydrochloride is similarly reported in U.S. Pat. No. 4,556,676, also to W. M. Welch, Jr. et al. The pure chiral trans-(1S)(4R)-N-methyl-4-(3,4-dichlorophenyl)-1,2,3,4-tetrahydro-1-naphthaleneamine starting material is also reported as a hydrochloride salt in the previously-mentioned paper by W. M. Welch, Jr. et al., along with the corresponding free amine base compound.

As previously indicated, the 2:1 (by weight) cis/trans-mixture of racemic N-methyl-4-(3,4-dichlorophenyl)-1,2,3,4-tetrahydro-1-naphthaleneamine isomers afforded as a final product of the process of this invention is valuable as an intermediate product that leads to the antidepressant agent known as sertraline or cis-(1S)(4S)-N-methyl-1,2,3,4-tetrahydro-1-naphthaleneamine. More specifically, when the aforesaid 2:1 (by weight) resultant cis/trans-mixture of racemic N-methyl-4-(3,4-dichlorophenyl)-1,2,3,4-tetrahydro-1-naphthaleneamine bases is first converted to the corresponding hydrochloride salts in an ethereal solvent system such as pure tetrahydrofuran, the pure crystalline racemic cis-amine salt exclusively separates from solution as a crystalline precipitate to afford pure racemic cis-N-methyl-4-(3,4-dichlorophenyl)-1,2,3,4-tetrahydro-1-naphthaleneamine hydrochloride, which is then recovered and converted back to the pure racemic cis-amine free base compound and subsequently resolved in a classical manner using the methods described by W. M. Welch, Jr. et al. in the aforesaid prior art to ultimately yield the desired pure cis-(1S)(4S)-N-methyl-4-(3,4-dichlorophenyl)-1,2,3,4-tetrahydro-1-naphthaleneamine (sertraline) as the hydrochloride salt. The corresponding 2:1 (by weight) cis/trans-mixture of chiral N-methyl-4-(3,4-dichlorophenyl)-1,2,3,4-tetrahydro-1-naphthaleneamine isomeric bases afforded as a final product of the process of this invention is similarly processed as an intermediate that leads to sertraline, except that the resolution step is not required since the desired pure chiral cis-(1S)(4S)-amine compound (sertraline) is obtained directly after isolation of the crystalline hydrochloride salt.

Hence, the novel process of the present invention now provides a way to convert unwanted trans-isomeric N-methyl-4-(3,4-dichlorophenyl)-1,2,3,4-tetrahydro-1-naphthaleneamine back to the desired pure cis-isomer (racemic or chiral) and thus to effectively recycle the previously unwanted trans-isomer back into the present method of production for obtaining said desired cis-isomer. The latter accomplishment, in turn, represents a major improvement over prior art methods in view of the increased ease and simplicity of operation, and the concomitant decrease in the total costs of production.

EXAMPLE 1

A mixture consisting of 5.0 g. (0.0164 mole) of racemic trans-N-methyl-4-(3,4-dichlorophenyl)-1,2,3,4-tetrahydro-1-naphthaleneamine [W. M. Welch et al., *Journal of Medicinal Chemistry*, Vol. 27, No. 11, p. 1508 (1984)] dissolved in 60 ml. of tetrahydrofuran, which also contained 3.09 ml. of tert.-butanol and 3.68 g. (0.0328 mole) of potassium tert.-butoxide, was heated to reflux for a period of 48 hours. Upon completion of this step, the solvent was removed by means of evaporation under reduced pressure and the resulting residue was thereafter taken up in methylene chloride and washed with three-successive 60 ml. portions of water, followed by drying over anhydrous magnesium sulfate. After removal of the drying agent by means of filtration and the solvent by means of evaporation under reduced pressure, there was finally obtained a residual oil which proved to be a 2:1 (by weight) mixture of the racemic cis- and trans-amines, as attested to by nuclear magnetic resonance data. When the latter oil was dissolved in tetrahydrofuran and subsequently treated with anhydrous hydrogen chloride gas, the cis-amine precipitated as the hydrochloride salt, while the trans-amine hydrochloride remained in solution. In this manner, there were ultimately obtained 3.5 g. (62%) of pure racemic cis-N-methyl-4-(3,4-dichlorophenyl)-1,2,3,4-tetrahydro-1-naphthaleneamine hydrochloride (m.p. 275°–277° C.) in the form of the recovered crystalline salt. The melting points reported in the literature for the pure racemic cis-amine hydrochloride and pure racemic trans-amine hydrochloride salts were 275°–277° C. and 214°–216° C., respectively, according to W. M. Welch et al. in the *Journal of Medicinal Chemistry*, Vol. 27, No. 11, p. 1508 (1984).

EXAMPLE 2

The procedure described in Example 1 was repeated except that 5.0 g. (0.0164 mole) of a 1:1 (by weight) mixture of pure racemic cis-N-methyl-4-(3,4-dichlorophenyl)-1,2,3,4-tetrahydro-1-naphthaleneamine and pure racemic trans-N-methyl-4-(3,4-dichlorophenyl)-1,2,3,4-tetrahydro-1-naphthaleneamine was the starting material employed in place of the corresponding pure trans-isomer alone, using the same molar proportions as before. In this particular case, the corresponding final product obtained was a residual oil which proved to be a 2:1 (by weight) mixture of the racemic cis- and trans-amines, substantially identical in every respect with the product of Example 1, as attested to by nuclear magnetic resonance data. Pure racemic cis-N-methyl-4-(3,4-dichlorophenyl-1,2,3,4-tetrahydro-1-naphthaleneamine hydrochloride (m.p. 275°–277° C.) was then isolated from the aforesaid mixture in the same manner as that already described for the same product in Example 1. In this instance, the yield of pure product amounted to 61%, based on the amount of starting material used.

EXAMPLE 3

The procedure described in Example 1 is repeated except that 5.0 g. (0.0164 mole) of a 1:9 (by weight) mixture of pure racemic cis-N-methyl-4-(3,4-dichlorophenyl)-1,2,3,4-tetrahydro-1-naphthaleneamine and pure racemic trans-N-methyl-4-(3,4-dichlorophenyl)-1,2,3,4-tetrahydro-1-naphthaleneamine is the starting material employed in lieu of the corresponding pure trans-isomer alone, using the same molar proportions as before. In this particular case, the corresponding final product obtained is a 2:1 (by weight) mixture of the racemic cis- and trans-amines, substantially identical in every respect with the product of Example 1. Pure racemic cis-N-methyl-4-(3,4-dichlorophenyl)-1,2,3,4-tetrahydro-1-naphthaleneamine hydrochloride is then isolated from the aforesaid mixture in the same manner as that already described for the identical product in Example 1.

EXAMPLE 4

The procedure described in Example 1 is repeated except that 5.0 g. (0.0164 mole) of a 1:4 (by weight) mixture of pure racemic cis-N-methyl-4-(3,4-dichlorophenyl)-1,2,3,4-tetrahydro- 1-naphthaleneamine and pure racemic trans-N-methyl-4-(3,4-dichlorophenyl)-1,2,3,4-tetrahydro-1-naphthaleneamine is the starting material employed in lieu of the corresponding pure trans-isomer alone, using the same molar proportions as before. In this particular case, the corresponding final product obtained is again a 2:1 (by weight) mixture of the racemic cis- and trans-amines, substantially identical in every respect with the product of Example 1. pure racemic cis-N-methyl-4-(3,4-dichlorophenyl)-1,2,3,4-tetrahydro-1-naphthaleneamine hydrochloride is then isolated from the aforesaid mixture in the same manner as that already described for the identical product in Example 1.

EXAMPLE 5

The procedure described in Example 1 is repeated except that 5.0 g. (0.0164 mole) of a 2:3 (by weight) mixture of pure racemic cis-N-methyl-4-(3,4-dichlorophenyl)-1,2,3,4-tetrahydro-1-naphthaleneamine and pure racemic trans-N-methyl-4-(3,4-dichlorophenyl)-1,2,3,4-tetrahydro-1-naphthaleneamine is the starting material employed in lieu of the corresponding pure trans-isomer alone, using the same molar proportions as before. In this particular case, the corresponding final product obtained is again a 2:1 (by weight) mixture of the racemic cis- and trans-amines, substantially identical in every respect with the product of Example 1. Pure racemic cis-N-methyl-4-(3,4-dichlorophenyl)-1,2,3,4-tetrahydro-1-naphthaleneamine hydrochloride is then isolated from the aforesaid mixture in the same manner as that already described for the identical product in Example 1.

EXAMPLE 6

The procedure described in Example 1 is repeated except that 5.0 g (0.0164 mole) of pure chiral trans-(1S)(4R)-N-methyl-4-(3,4-dichlorophenyl)-1,2,3,4-tetrahydro-1-naphthaleneamine [W. M. Welch et al., *Journal of Medicinal Chemistry*, Vol. 27, No. 11, p. 1508 (1984)] is the starting material employed in place of the pure racemic trans-N-methyl- 4-(3,4-dichlorophenyl)-1,2,3,4-tetrahydro-1-naphthalene, using the same molar proportions as before. In this particular case, the corresponding final product obtained is a 2:1 (by weight) mixture of chiral cis-(1S)(4S)-N-methyl-4-(3,4-dichlorophenyl)-1,2,3,4-tetrahydro-1-naphthaleneamine (sertraline) and chiral trans-(1S)(4R)-N-methyl-4-(3,4-dichlorophenyl)-1,2,3,4-tetrahydro-1-naphthaleneamine. Pure chiral cis-(1S)(4S)-N-methyl-4-(3,4-dichlorophenyl)-1,2,3,4-tetrahydro-1-naphthaleneamine hydrochloride (sertraline hydrochloride) is then isolated from the aforesaid mixture in the same manner as that described previously for the corresponding racemic salt reported in Example 1.

EXAMPLE 7

The procedure described in Example 6 is repeated except that 5.0 g (0.0164 mole) of a 1:1 (by weight) mixture of pure chiral cis-(1S)(4S)-N-methyl-4-(3,4-dichlorophenyl)-1,2,3,4-tetrahydro-1-naphthaleneamine and pure chiral trans-(1S)(4R)-N-methyl-4-(3,4-dichlorophenyl)-1,2,3,4-tetrahydro-1-naphthaleneamine is the starting material employed in place of the corresponding pure trans-isomer alone, using the same molar proportions as before. In this particular case, the corresponding final product obtained is a 2:1 (by weight) mixture of the chiral cis-(1S)(4S)- and chiral trans-(1S)(4R)-amines, substantially identical in every respect with the product of Example 6. Pure chiral cis-(1S)(4S)-N-methyl-4-(3,4-dichlorophenyl)-1,2,3,4-tetrahydro-1-naphthaleneamine hydrochloride (sertraline hydrochloride) is then isolated from the aforesaid mixture in the same manner as that described previously for the corresponding racemic salt reported in Example 1.

I claim:

1. A process for converting trans-isomeric N-methyl-4-(3,4-dichlorophenyl)-1,2,3,4-tetrahydro-1-naphthaleneamine to cis-isomeric N-methyl-4-(3,4-dichlorophenyl)-1,2,3,4-tetrahydro-1-naphthaleneamine, which comprises contacting trans-isomeric N-methyl-4-(3,4-dichlorophenyl)-1,2,3,4-tetrahydro-1-naphthaleneamine in the absence or presence of up to about an equal part by weight of the corresponding cis-isomer with a basic equilibration agent in a reaction-inert polar organic solvent system at a temperature that is in the range of from about 55° C. up to about 125° C. until the amount of the desired cis-amine in the resultant cis/trans-mixture achieves a constant value of about 2:1 on a weight-by-weight basis.

2. A process for converting racemic trans-N-methyl-4-(3,4-dichlorophenyl)-1,2,3,4-tetrahydro-1-naphthaleneamine to the corresponding cis-isomeric product, which comprises contacting racemic trans-N-methyl-4-(3,4-dichlorophenyl)-1,2,3,4-tetrahydro-1-naphthaleneamine in the absence or presence of up to about an equal part by weight of the corresponding cis-isomer with a basic equilibration agent in a reaction-inert polar organic solvent system at a temperature that is in the range of from about 55° C. to about 125° C. until the amount of the desired cis-amine in the resultant cis/trans-mixture achieves a constant value of about 2:1 on a weight-by-weight basis.

3. A process for converting chiral trans-(1S)(4R)-N-methyl-4-(3,4-dichlorophenyl)-1,2,3,4-tetrahydro-1-naphthaleneamine to the corresponding cis-isomeric product, which comprises contacting chiral trans-(1S)(4R)-N-methyl-4-(3,4-dichlorophenyl)-1,2,3,4-tetrahydro-1-naphthaleneamine in the absence or presence of up to about an equal part by weight of the corresponding cis-isomer with a basic equilibration agent in a reaction-inert polar organic solvent system at a temperature of from about 55° C. to up about 125° C. until the amount of the desired cis-amine in the resultant cis/trans-mixture achieves a constant value of about 2:1 on a weight-by-weight basis.

4. A process as claimed in claim 2 wherein racemic trans-N-methyl-4-(3,4-dichlorophenyl)-1,2,3,4-tetrahydro-1-naphthaleneamine is the starting material employed in the absence of any substantial amount of the corresponding cis-isomer.

5. A process as claimed in claim 2 wherein a 1:1 cis/trans-mixture consisting of about equal, parts by weight of racemic cis- and racemic trans-N-methyl-4-(3,4-dichlorophenyl)-1,2,3,4-tetrahydro-1-naphthaleneamine is the starting material employed.

6. A process as claimed in claim 3 wherein chiral trans-(1S)(4R)-N-methyl-4-(3,4-dichlorophenyl)-1,2,3,4-tetrahydro-1-naphthaleneamine is the starting material employed in the absence of any substantial amount of the corresponding cis-isomer.

7. A process as claimed in claim 3 wherein a 1:1 cis/trans-mixture consisting of about equal parts by weight of chiral cis-(1S)(4S]-N-methyl-4-(3,4-dichlorophenyl)-1,2,3,4-tetrahydro-1-naphthaleneamine and chiral trans-(1S)(4R)-N-methyl-4-(3,4-dichlorophenyl)-1,2,3,4-tetrahydro-1-naphthaleneamine is the starting material employed.

8. A process as claimed in claim 1 wherein the basic equilibration agent employed is 1,8-diazabicyclo[5.4.0]undec-7-ene.

9. A process as claimed in claim 1 wherein the basic equilibration agent employed is an, alkali metal lower alkoxide ($C_1$–$C_4$).

10. A process as claimed in claim 9 wherein the alkali metal lower alkoxide is potassium tert.-butoxide.

11. A process as claimed in claim 1 wherein an excess in moles of the equilibration agent is employed with respect to the total amount of N-methyl-4-(3,4-dichlorophenyl)-1,2,3,4-tetrahydro-1-naphthaleneamine starting material.

12. A process as claimed in claim 11 wherein the molar ratio of the N-methyl-4-(3,4-dichlorophenyl)-1,2,3,4-tetrahydro-1-naphthaleneamine starting material to the basic equilibration agent is in the range of from about 1.0:1.0 to about 1.0:3.0, respectively.

13. A process as claimed in claim 12 wherein the molar ratio of N-methyl-4-(3,4-dichlorophenyl)-1,2,3,4-tetrahydro-1-naphthaleneamine starting material to the basic equilibration agent is about 1.0:2.0.

14. A process as claimed in claim 1 wherein the reaction-inert polar organic solvent is a lower N,N-dialkyl lower alkanoamide having a total of up to six carbon atoms with at least one of said atoms always being present in the N,N-unsubstituted alkanoamide moiety.

15. A process as claimed in claim 14 wherein the lower N,N-dialkyl lower alkanoamide is dimethylformamide.

16. A process as claimed in claim 1 wherein the reaction-inert polar organic solvent is tetrahydrofuran or a mixture of same with a minor amount of tert.-butanol.

17. A process as claimed in claim 1 wherein the basic equilibration agent is 1,8-diazabicyclo[5.4.0]undec-7-ene and the reaction-inert polar organic solvent is dimethylformamide.

18. A process as claimed in claim 1 wherein the basic equilibration agent is potassium tert.-butoxide and the reaction-inert polar organic solvent is tetrahydrofuran or a mixture of the same with a minor amount of tert.-butanol.

19. A process as claimed in claim 18 wherein the basic equilibration reaction is conducted at a temperature of from about 65° C. to about 90° C. for a period of at least about four hours.

20. A process as claimed in claim 4 wherein pure racemic cis-N-methyl-4-(3,4-dichlorophenyl)-1,2,3,4-tetrahydro-1-naphthaleneamine is recovered from the resultant 2:1 cis/trans-mixture in the form of a hydrohalide salt.

21. A process as claimed in claim 20 wherein the hydrohalide salt recovered is pure racemic cis-N-methyl-4-( 3,4-dichlorophenyl)-1,2,3,4-tetrahydro-1-naphthaleneamine hydrochloride.

22. A process as claimed in claim 6 wherein pure chiral cis-(1S)(4S)-N-methyl-4-(3,4-dichlorophenyl)-1,2,3,-4-tetrahydro-1-naphthaleneamine is recovered from the resultant 2:1 cis/trans-mixture in the form of a hydrohalide salt.

23. A process as claimed in claim 20 wherein the hydrohalide salt recovered is pure chiral cis-(1S)(4S)-N-methyl-4-(3,4-dichlorophenyl)-1,2,3,4-tetrahydro-1-naphthaleneamine hydrochloride.

* * * * *